United States Patent [19]

Broadhurst et al.

[11] Patent Number: 5,731,441
[45] Date of Patent: Mar. 24, 1998

[54] HYDROXAMIC ACID DERIVATIVES WITH TRICYCLIC SUBSTITUTION

[75] Inventors: Michael John Broadhurst, Royston; Paul Anthony Brown; William Henry Johnson, both of Hitchin, all of England

[73] Assignee: Hoffmann-La Roche Inc., Nutley, N.J.

[21] Appl. No.: 741,158

[22] Filed: Oct. 29, 1996

Related U.S. Application Data

[62] Division of Ser. No. 417,317, Apr. 5, 1995.

[30] Foreign Application Priority Data

Apr. 25, 1994 [GB] United Kingdom ............ 9408183
Jan. 30, 1995 [GB] United Kingdom ............ 9501737

[51] Int. Cl.$^6$ .................. C07D 285/10; C07D 209/32; C07D 211/36; C07D 265/26
[52] U.S. Cl. ............ 548/135; 548/144; 548/226; 548/263.4; 548/317.1; 548/512; 548/513; 548/314.7; 546/242; 546/18; 546/210; 544/94; 544/286; 544/55; 544/56; 544/122; 544/370; 540/450; 540/597; 540/602
[58] Field of Search ............... 544/370, 122, 544/55, 56, 94, 286; 546/210, 18, 242; 548/314.7, 135, 144, 226, 263.4, 317.1, 512, 513; 540/597, 602, 450

[56] References Cited

U.S. PATENT DOCUMENTS

| | | | |
|---|---|---|---|
| 4,611,064 | 9/1986 | Schefczik | 548/484 |
| 5,318,964 | 6/1994 | Broadhurst et al. | 514/228.2 |
| 5,536,434 | 7/1996 | Venturello et al. | 510/375 |

FOREIGN PATENT DOCUMENTS

| | | |
|---|---|---|
| 0405788 | 1/1991 | European Pat. Off. |
| 0489577 | 6/1992 | European Pat. Off. |
| 0574758 | 12/1993 | European Pat. Off. |
| 0575844 | 12/1993 | European Pat. Off. |
| 0613883 | 9/1994 | European Pat. Off. |
| 90051716 | 5/1990 | WIPO |
| 9102716 | 3/1991 | WIPO |
| 9422309 | 10/1994 | WIPO |

OTHER PUBLICATIONS

Zanger, et al., "Structure–Activity Relationship and Drug Design", Remington's Pharmaceutical Science, Osol et al. ed., 16th ed., Philadelphia College of Pharmacy and Science, pp. 420–435 (1980).

*Primary Examiner*—Mukund J. Shah
*Assistant Examiner*—Tamthom T. Ngo
*Attorney, Agent, or Firm*—George W. Johnston; Dennis P. Tramaloni; Joseph P. Kirk, Jr.

[57] ABSTRACT

The invention provides hydroxamic acid derivatives of the general formula

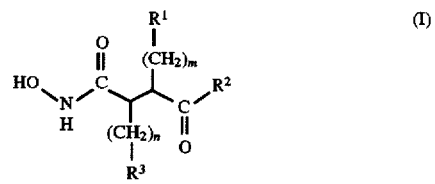

wherein $R^1$ represents cyclopropyl, cyclobutyl, cyclopentyl or cyclohexyl; $R^2$ represents a saturated 5- to 8-membered monocyclic or bridged N-heterocyclic ring, which N-heterocyclic ring is attached via the N atom and when it is monocyclic, optionally contains $NR^4$, O, S, SO or $SO_2$ as a ring member and/or is optionally substituted on one or more C atoms by hydroxy, lower alkyl, lower alkoxy, oxo, ketalized oxo, amino, mono(lower alkyl)amino, di(lower alkyl)amino,carboxy, lower alkoxycarbonyl, hydroxymethyl, lower alkoxymethyl, carbamoyl, mono(lower alkyl)-carbamoyl, di(lower alkyl)carbamoyl or hydroxyimino; $R^3$ represents a 5- or 6-membered N-heterocyclic ring which (a) is attached via the N atom, (b) optionally contains N, O and/or S, SO or $SO_2$ as an additional ring member, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl or aryl; $R^4$ represents hydrogen, lower alkyl, aryl, aralkyl or a protecting group; m stands for 1 or 2 and n stands for 1–4, pharmaceutically acceptable salts thereof, intermediates used in the manufacture thereof, and methods of use therefor. Compounds of formula I are collagenase inhibitors useful in the control or prevention of degenerative joint diseases such as rheumatoid arthritis and osteoarthritis or in the treatment of invasive tumours, atherosclerosis or multiple sclerosis.

1 Claim, No Drawings

HYDROXAMIC ACID DERIVATIVES WITH TRICYCLIC SUBSTITUTION

This is a division of application Ser. No. 08/417,317 filed Apr. 5, 1995.

SUMMARY OF THE INVENTION

The present invention is concerned with hydroxamic acid derivatives with tricyclic substitution.

The hydroxamic acid derivatives provided by the present invention are compounds of the general formula

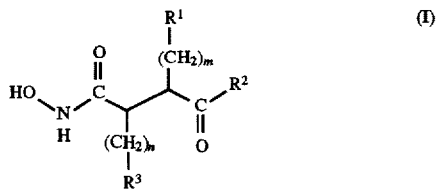

wherein
- $R^1$ represents cyclopropyl, cyclobutyl, cyclopentyl or cyclohexyl;
- $R^2$ represents a saturated 5- to 8-membered monocyclic or bridged N- heterocyclic ring which is attached via the N atom and which N-heterocyclic ring, when it is monocyclic, optionally contains $NR^4$, O, S, SO or $SO_2$ as a ring member and/or is optionally substituted on one or more C atoms by hydroxy, lower alkyl, lower alkoxy, oxo, ketalized oxo, amino, mono(lower alkyl) amino, di(lower alkyl) amino, carboxy, lower alkoxycarbonyl, hydroxymethyl, lower alkoxymethyl, carbamoyl, mono(lower alkyl)-carbamoyl, di(lower alkyl)carbamoyl or hydroxyimino;
- $R^3$ represents a 5- or 6-membered N-heterocyclic ring which (a) is attached via the N atom, (b) optionally contains N, O and/or S, SO or $SO_2$ as an additional ring member, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl or aryl;
- $R^4$ represents hydrogen, lower alkyl, aryl, aralkyl or a protecting group;
- m stands for 1 or 2; and
- n stands for 1–4;

and pharmaceutically acceptable salts thereof.

The compounds of formula I possess valuable pharmacological properties. In particular, they are collagenase inhibitors and can used in the control or prevention of degenerative joint diseases such as rheumatoid arthritis and osteoarthritis or in the treatment of invasive tumours, atherosclerosis or multiple sclerosis.

Objects of the present invention are the compounds of formula I and their pharmaceutically acceptable salts per se; a process for the manufacture of said compounds and salts; intermediates useful in said process; and the use of said compounds and salts in the control or prevention of illnesses or in the improvement of health, especially in the control or prevention of degenerative joint diseases or in the treatment of invasive tumours or atherosclerosis.

DETAILED DESCRIPTION OF THE INVENTION

The hydroxamic acid derivatives provided by the present invention are compounds of the general formula

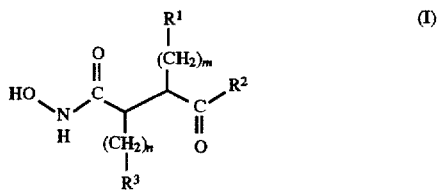

wherein $R^1$, $R^2$, $R^3$ m and n are hereinbefore described.

As used in this Specification, the term "lower alkyl", alone or in combination, means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. The term "lower alkoxy", alone or in combination, means a straight-chain or branched-chain alkoxy group containing a maximum of six carbon atoms, such as methoxy, ethoxy, n-propoxy, isopropoxy, n-butoxy, tert.butoxy and the like. The term "aryl" means an unsubstituted or substituted aromatic group, such as phenyl, which is optionally substituted by, for example, lower alkyl, lower alkoxy and/or halogen, i.e. fluorine, chlorine, bromine or iodine. As examples of aryl groups that may be used in accordance with this invention, p-tolyl, p-methoxyphenyl, p-chlorophenyl and the like can be enumerated. The term "aralkyl" means a lower alkyl group as hereinbefore defined in which one or more hydrogen atoms is/are replaced by aryl group as hereinbefore defined. Any aralkyl can be used in accordance with this invention, such as benzyl and the like. A ketalized oxo group can be any ketal compound containing a carbon with two oxygen atoms, for example, ethylenedioxy.

A protecting group denoted by $R^4$ can be any conventional protecting group, e.g. as known in peptide chemistry, such as benzyloxycarbonyl, tert.butoxycarbonyl, acetyl and the like.

As used in this Specification, N-heterocyclic denotes compounds having one or more ring structures, wherein at least one ring structure is represented by an N atom. The term "monocyclic N-heterocyclic" denotes an N-heterocyclic group having one ring structure. As used herein the term "bridged N-heterocyclic ring" denotes a heterocyclic ring structure containing at least one N atom, which is fused or bridged to at least one additional ring structure.

Examples of monocyclic N-heterocyclic rings denoted by $R^2$ are 1-pyrrolidinyl, piperidino, 1-piperazinyl, 4-aryl-1-piperazinyl, hexahydro-1-pyridazinyl, morpholino, tetrahydro-1,4-thiazin-4-yl, tetrahydro-1,4-thiazin-4-yl 1-oxide, tetrahydro-1,4-thiazin-4-yl 1,1-dioxide, thiazolidin-3-yl, hexahydroazepino and octahydroazocino which can be substituted in the manner given earlier; for example 2-(methylcarbamoyl)-1-pyrrolidinyl, 2-(hydroxymethyl)-1-pyrrolidinyl, 4-hydroxypiperidino, 2-(methylcarbamoyl)piperidino, 4-hydroxyiminopiperidino, 4-methoxypiperidino, 4-methyl-1-piperazinyl, 4-phenyl-1-piperazinyl, 1,4-dioxa-8-azaspiro[4.5]decan-8-yl, hexahydro-3-(methylcarbamoyl)-2-pyridazinyl, hexahydro-1-(benzyloxycarbonyl)-2-pyridazinyl, 5,5-dimethyl-4-methylcarbamoyl-thiazolidin-3-yl and 5,5-dimethyl-4-propylcarbamoyl-thiazolidin-3 -yl.

Examples of bridged N-heterocyclic rings denoted by $R^2$ are 5-azabicyclo[2.1.1]hexane, 3-azabicyclo[3.1.1]heptane, 7-azabicyclo[2.2.1]-heptane, 3-azabicyclo[3.2.1]octane, 2-azabicyclo[3.2.2]nonane and 3-azabicyclo[3.2.2]nonane.

Examples of N-heterocyclic rings denoted by $R^3$ are rings of the formulae:

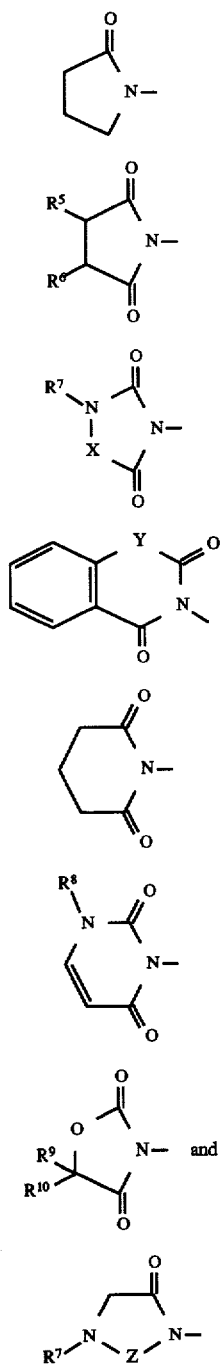

in which

R⁵ and R⁶ each represent hydrogen or together represent an additional bond or the remainder of a fused benzene ring;

R⁷ represents hydrogen, lower alkyl, on aryl; and

X represents —CO—, —CH₂—, —CH(lower alkyl)—, —C(lower alkyl)₂—, —NH—, —N(lower alkyl)— or —O—; or, when R⁷ represents lower alkyl and X represents —N(lower alkyl)—, the lower alkyl groups can be joined to form a 5-, 6- or 7-membered ring;

R⁸ represents hydrogen, lower alkyl or aryl;

R⁹ and R¹⁰ each represent hydrogen or lower alkyl;

Y represents —O—, —NH— or —N(lower alkyl)—; and

Z represents S, SO or SO₂;

wherein lower alkyl and aryl is as hereinbefore defined.

Examples of such N-heterocyclic ring denoted by R³ are 2-oxo-1-pyrrolidinyl, 2,5-dioxo-1-pyrrolidino, phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2,6-dioxopiperidino, 5,5-dimethyl-2,4-dioxo-3-oxazolidinyl and hexahydro-1,3-dioxopyrazolo[1,2-a][1,2,4]triazol-2-yl.

One group of preferred compounds Of formula I comprises those in which R² represents 1-pyrrolidinyl, piperidino, 4-aryl-1-piperazino, morpholino, tetrahydro-1,4-thiazin-4-yl, tetrahydro-1,4-thazin-4-yl 1,1-dioxide, thiazolidin-3-yl, hexahydroazepino or octahydroazocino optionally substituted on one or more C atoms by hydroxy, lower alkyl, lower alkoxy, ketalized oxo or mono(lower alkyl)-carbamoyl. The preferred R² is piperidino which is optionally substituted by hydroxy, particularly 4-hydroxypiperidino. Another preferred R² is 3-azabicyclo[3.2.2]nonane. Also preferred are compounds of formula I in which R³ represents a group of formula (b), (c), or (h). When R³ represents a group of formula (c), R⁷ is preferably lower alkyl and X is preferably —C(lower alkyl)₂—, particularly 3,4,4-trimethyl-2,5-dioxo-1-imidazolidinyl. Preferably, m and n both stand for 1.

The most preferred compounds of formula I are:

1-[3-cyclopropyl-2(R)-[1(R or S)-(hydroxycarbamoyl)-2-(3,4,4-trimethyl-2,5-dioxo-1-imidazolidinyl)ethyl]propionyl]piperidine, 1-[3-cyclopropyl-2-(R)-[1(R or S)-(hydroxycarbamoyl)-2-(3,4,4-trimethyl-2,5-dioxo-1-imidazolidinyl)ethyl]propionyl]-4-piperidinol, 3-[3-cyclopropyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]nonane, 1-[3-cyclobutyl-2(R)-[1(R or S)-(hydroxycarbamoyl)-2-(3,4,4-trimethyl-2,5-dioxo-1-imidazolidinyl)ethyl]propionyl]piperidine, 1-[3-cyclobutyl-2(R)-[1(R or S)-(hydroxycarbamoyl)-2-(3,4,4-trimethyl-2,5-dioxo-1-imidazolidinyl)ethyl]propionyl]-4-piperidinol, 3-[3-cyclobutyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]nonane, 1-[3-cyclopentyl-2[(R)-[1(R or S)-(hydroxycarbamoyl)-2-(3,4,4-trimethyl-2,5-dioxo-1-imidazolidinyl)ethyl]propionyl]-4-piperidinol, 3-[3-cyclopentyl-2(R)-[1(R or S)-(hydroxycarbamoyl)-2-[3,4,4-trimethyl-2,5-dioxo-1-imidazolidinyl)ethyl]propionyl]-3-azabicyclo[3.2.2]nonane and 1-[3-cyclopentyl-2(R)-[1(R or S)-(hydroxycarbamoyl)-2-(3,4,4-trimethyl-2,5-dioxo-1-imidazolidinyl)ethyl]propionyl]piperidine.

Other preferred compounds of formula I hereinbefore are:

1-[3-cyclohexyl-2(R)-[1(R or S)-(hydroxycarbamoyl)-2-(3,4,4-trimethyl-2,5-dioxo-1-imidazolidinyl)ethyl]propionyl]piperidine, 4-[3-cyclopentyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine, 4-[3-cyclopentyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine S,S-dioxide, 4-[3-cyclobutyl-2(R)-[1(R or S)-(hydroxycaxbamoyl)-2-(3,4,4-trimethyl-2,5-dioxo-1-imidazolidinyl)ethyl]propionyl]tetrahydro-1,4-thiazine, 4-[3-cyclohexyl-2(R)-[1(R or S)-(hydroxycarbamoyl)-2-(3,
4,4-trimethyl-2,5-dioxo-1-imidazolidinyl)ethyl]
propionyl]tetrahydro-1,4-thiazine, 3-[3-cyclopentyl-2(R)-[1(R or S)-(hydroxycarbamoyl)-2-(3,
4,4-trimethyl-2,5-dioxo-1-imidazolidinyl)ethyl]
propionyl]-5,5-dimethyl-N-propyl-4(R)-
thiazolidinecarboxamide, 4-[3-cyclopentyl-2(R)-[1(R or S)-(hydroxycarbamoyl)-2-(3,
4,4-trimethyl-2,5-dioxo-1-imidazolidinyl)ethyl]
propionyl]morpholine, 3-[3-cyclopentyl-2(R)-[1(R or S)-(hydroxycarbamoyl)-2-(3,
4,4-trimethyl-2,5-dioxo-1-imidazolidinyl)ethyl]
propionyl]-N,5,5-trimethyl-4(R)-
thiazolidinecarboxamide, 4-[3-cyclobutyl-2(R)-[1(R or S)-(hydroxycarbamoyl)-2-(3,
4,4-trimethyl-2,5-dioxo-1-imidazolidinyl)ethyl]
propionyl]-4-phenylpiperazine, 4-[3-cyclobutyl-2(R)-[1(R or S)-(hydroxycarbamoyl)-2-(3,
4,4-trimethyl-2,5-dioxo-1-imidazolidinyl)ethyl]
propionyl]morpholine, 1-[3-cyclobutyl-2(R)-[1(R or S)-(hydroxycarbamoyl)-2-(3,
4,4-trimethyl-2,5-dioxo-1-imidazolidinyl)ethyl]
propionyl]pyrrolidine, 8-[3-cyclobutyl-2(R)-[1(R or S)-(hydroxycarbamoyl)-2-(3,
4,4-trimethyl-2,5-dioxo-1-imidazolidinyl)ethyl]
propionyl]-1,4-dioxa-8-azaspiro[4,5]decane, 1-[3-cyclobutyl-2(R)-[1(R or S)-(hydroxycarbamoyl)-2-(3,
4,4-trimethyl-2,5-dioxo-1-imidazolidinyl)ethyl]
propionyl]-4-methoxypiperidine, 1-[3-cyclobutyl-2(R)-[1(R or S)-(hydroxycarbamoyl)-2-(3,
4,4-trimethyl-2,5-dioxo-1-imidazolidinyl)ethyl]
propionyl]octahydroazocine, 1-[3-cyclobutyl-2(R)-[1(R or S)-(hydroxycarbamoyl)-2-(5,
5-dimethyl-2,4-dioxo-3-oxazolidinyl)ethyl]propionyl]
piperidine, 1-[3-cyclobutyl-2(R)-[1(R or S)-(hydroxycarbamoyl)-2-(3,
4,4-trimethyl-2,5-dioxo-1-imidazolidinyl)ethyl]
propionyl]-hexahydroazepine, 1-[3-cyclobutyl-2(R)-[2-(hexahydro-1,3-dioxopyrazolo[1,
2-a][1,2,4]triazol-2-yl)-1(R or S)-(hydroxycarbamoyl)
ethyl]propionyl]piperidine and 1-[3-cyclobutyl-2(R)-[1(R or S)-(hydroxycarbamoyl)-2-
phthalimidoethyl]propionyl]piperidine.

The compounds of formula I form pharmaceutically acceptable salts with bases such as alkali metal hydroxides (e.g. sodium hydroxide and potassium hydroxide), alkaline earth metal hydroxides (e.g. calcium hydroxide and magnesium hydroxide), ammonium hydroxide and the like. The compounds of formula I which are basic form pharmaceutically acceptable salts with acids. As such salts there come into consideration not only salts with inorganic acids such as hydrohalic acids (e.g. hydrochloric acid and hydrobromic acid), sulphuric acid, nitric acid, phosphoric acid etc, but also salts with organic acids such as acetic acid, tartaric acid, succinic acid, fumaric acid, maleic acid, malic acid, salicylic acid, citric acid, methanesulphonic acid, p-toluenesulphonic acid, etc.

The compounds of formula I contain at least two asymmetric carbon atoms and can accordingly exist as optically active enantiomers, a diastereoisomers or as racemates. The present invention is intended to embrace all of these forms.

According to the process provided by the present invention, the compounds of formula I and their pharmaceutically acceptable salts are manufactured by (a) reacting an acid of the general formula

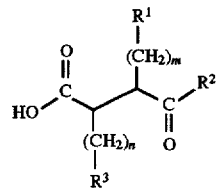

wherein $R^1$, $R^2$, $R^3$, m and n have the significance given earlier, with a compound of the general formula $H_2N—OZ$ (III)

wherein Z represents hydrogen, tri(lower alkyl)silyl or diphenyl(lower alkyl)silyl, and, where required, cleaving off any diphenyl(lower alkyl) silyl group present in the reaction product or (b) catalytically hydrogenating a compound of the general formula

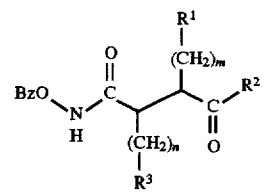

wherein $R^1$, $R^2$, $R^3$, m and n have the significance given earlier and Bz represent benzyl, and if desired, converting a compound of formula I obtained into a pharmaceutically acceptable salt.

The reaction of an acid of formula II with a compound of formula III in accordance with embodiment (a) of the process can be carried out in a known manner. For example, an acid of formula II can be reacted with a compound of formula III in an inert organic solvent such as dichloromethane, dimethylformamide or the like using 1-hydroxybenzotriazole in the presence of a condensation agent such as 1-ethyl-3-(3-dimethylaminopropyl) carbodiimide hydrochloride at about 0° C. to about room temperature. Alternatively, an acid of formula II can be converted into the corresponding acid chloride (e.g. using oxalyl chloride) and the acid chloride can then be reacted with a compound of formula III. Preferred compounds of formula III are those in which Z represents tert.butyldimethylsilyl or tert.butyldiphenylsilyl. When a compound of formula III in which Z represents tri(lower alkyl)silyl is used, this group is cleaved off during the reaction and working-up, and a compound of formula I is obtained directly. On the other hand, when a compound of formula III in which Z represents diphenyl(lower alkyl)silyl is used, this group remains in the reaction product and must subsequently be cleaved off in a known manner, for example by means of fluoride ions.

The catalytic hydrogenation of a compound of formula IV in accordance with embodiment (b) of the process can be carried out in a manner known per se; for example in an inert organic solvent using hydrogen in the presence of a noble metal catalyst. Suitable inert organic solvents are, for example, lower alkanols such as methanol, ethanol, etc. With respect to the catalyst, this can be, for example, a platinum, palladium or rhodium catalyst which can be supported on a suitable carrier material. Palladium-oncharcoal is the preferred catalyst. The temperature and pressure are not critical, although for convenience the catalytic hydrogenation is preferably carried out at room temperature and under atmospheric pressure.

Compounds of formula I can be converted into pharmaceutically acceptable salts by treatment with bases and basic compounds of formula I can be converted into pharmaceutically acceptable salts by treatment with acids. Such treatments can be carried out in a conventional manner.

The acids of formula II which are used as starting materials in embodiment (a) of the process are novel and form a further object of the present invention.

The acids of formula II can be prepared, for example, as illustrated in the following Reaction Scheme in which $R^1$, $R^2$, $R^3$, m and n have the significance given earlier, Bz represents benzyl and tBu represents tert-butyl:

of formula V, which can obtained according to the procedure described by Chenault H. K., Dahmer J. and Whitesides G. M., J.Am. Chem. Soc. 1989, 111, 6354–6364, is convened by treatment with sodium nitrite in the presence of concentrated sulphuric acid into a hydroxy acid of formula VI which is subsequently reacted with benzyl bromide in the presence of an organic base e.g. a trialkylamine such as triethylamine, into a corresponding benzyl ester of formula VII. The latter is then activated, e.g. by reaction with trifluoromethanesulphonic anhydride, and treated with benzyl tert-butyl malonate in the presence of a strong base, e.g. an alkali metal hydride such as sodium hydride, to give a compound of formula VIII. Treatment of the latter with a strong base, e.g. an alkali metal hydride such as sodium hydride, and reaction with a compound of formula IX yields a dibenzyl tert-butyl butanetricarboxylate of formula X

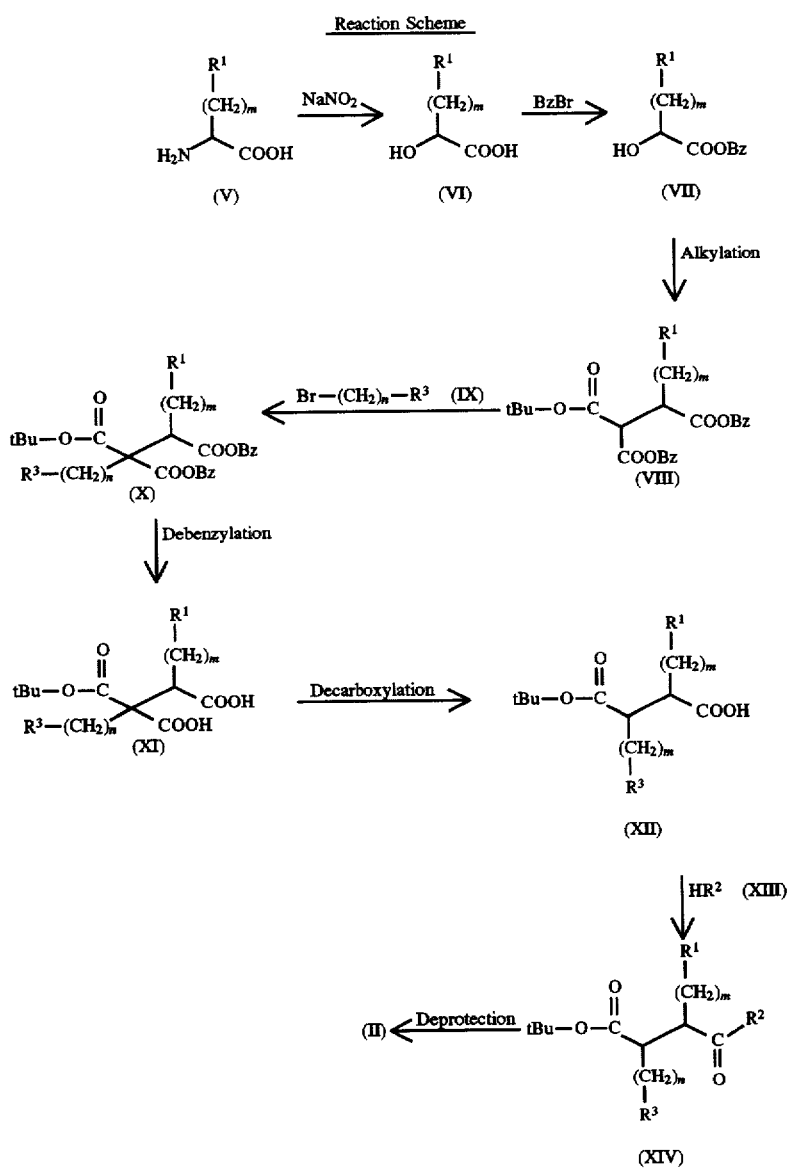

Having regard to the foregoing Reaction Scheme, the individual steps thereof can be carried out according to methods known per se. Thus, in the first step, an amine acid which is then debenzylated by catalytic hydrogenation, e.g. in the presence of a palladium catalyst such as palladium-on-charcoal, to give a tert-butyl dihydrogen butanetricarboxylate of formula XI. Decarboxylation of this compound, e.g. by heating in toluene with triethylamine, which may be carried out in situ, yields a tert-butyl hydrogen succinate of formula XII which is condensed with a cyclic amine of formula XIII, e.g. according to the acid chloride method or using 1-hydroxybentriazole in the presence of a condensation agent such as 1-ethyl-3-(3-dimethylaminopropyl) carbodiimide hydrochloride, to give a compound of formula XIV which is deprotected (e.g. by treatment with trifluoroacetic acid) to give an acid of formula II.

The compounds of formula IV which are used as starting materials in embodiment (b) of the process are novel and form a further object of the present invention.

The compounds of formula IV can be prepared, for example reacting an acid of formula II with O-benzylhydroxylamine. This reaction can be carried out in a known manner, for example in an inert organic solvent such as dichloromethane or dimethylformamide using 1-hydroxybenzotriazole in the presence of a condensation agent such as 1-ethyl-3-(3-dimethylaminopropyl) carbodiimide hydrochloride.

The remaining compounds which are used as intermediates or reactants in the manufacture of the compounds of formula I are known compounds or analogues of known compounds which can be prepared in a similar manner to the known compounds.

As mentioned earlier, the compounds of formula I and their pharmaceutically acceptable salts are collagenase inhibitors. The in vitro collagenase inhibiting activity of the present compounds and salts can be demonstrated by known means using collagenase obtained from a culture of human synovial fibroblasts according to the method of Dayer J-M et al., Proc. Natl. Acad. Sci. USA (1976), 73 945, following activation of the pro-collagenase in the conditioned medium by treatment with trypsin. Collagenase activity can be measured using $^{14}C$-acetylated collagen type I from rat tail tendons as the substrate and employing the microtitre plate assay method of Johnson-Wint, B, Anal. Biochem. (1980); 104, 175. The $IC_{50}$ measured by this assay is a measure of the collagenase inhibiting activity and is that concentration of a compound or salt of the present invention in the enzyme digestion which reduced substrate cleavage and solubilization to 50% of that achieved by the enzyme alone. An $IC_{50}$ measured means by this assay that the compound or salt has collagenase inhibiting activity. This is true regardless of the value of the $IC_{50}$.

The results obtained in the foregoing test with representative compounds and salts of this invention are compiled in Table I hereinafter:

TABLE I

| Product of Example No. | $IC_{50}$ (nM) |
|---|---|
| 2 | 18.0 |
| 4 | 7.0 |
| 5 | 2.5 |
| 7 | 6.5 |
| 9 | 8.5 |
| 16 | 4.1 |
| 17 | 2.35 |
| 23 | 34.0 |

The compounds of formula I and their pharmaceutically acceptable salts can be used as medicaments, for example in the form of pharmaceutical preparations. The pharmaceutical preparations can be administered orally, e.g. in the form of tablets, coated tablets, dragées, hard and soft gelatine capsules, solutions, emulsions or suspensions. However, they can also be administered rectally, e.g. in the form of suppositories, or parenterally, e.g. in the form of injection solutions.

For the manufacture of pharmaceutical preparations the compounds of formula I and their pharmaceutically acceptable salts can be formulated with therapeutically inert, inorganic or organic carriers. Lactose, corn starch or derivatives thereof, talc, stearic acid or its salts can be used, for example, as such carriers for tablets, coated tablets, dragées and hard gelatine capsules. Suitable carriers for salts gelatine capsules are, for example, vegetable oils, waxes, fats, semisolid and liquid polyols and the like. Depending on the nature of the active ingredient no carriers are, however, generally required in the case of soft gelatine capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerine, vegetable oils and the like. Natural and hardened oils, waxes, fats, semi-liquid polyols and the like are suitable carriers for the manufacture of suppositories.

The pharmaceutical preparations can also contain preservatives, stabilizers, wetting agents, emulsifiers, sweeteners, colorants, flavorants, salts for adjustment of the osmotic pressure buffers coating agents or antioxidants.

Medicaments containing a compound of formula I or a pharmaceutically acceptable salt thereof and a therapeutically acceptable carrier as well as a process for the manufacture of such medicaments are also objects of the present invention. This process comprises mixing a compound of formula I or a pharmaceutically acceptable salt thereof with a therapeutically inert carrier material and bringing the mixture into a galenical administration form.

As mentioned earlier, the compounds of formula I and their pharmaceutically acceptable salts can be used in the control or prevention of illnesses, especially in the control or prevention of degenerative joint diseases or in the treatment of invasive tumours, atherosclerosis or multiple sclerosis. The dosage can vary within wide limits and will, of course, be adjusted to the individual requirements in each particular case. In general, in the case of administration to adults, a daily dosage of from about 5 mg to about 30 mg, preferably from about 1 mg to about 15 mg, should be appropriate, although the upper limit may be exceeded when this is found to be expedient. The daily dosage can be administered as a single dosage or in divided dosages.

The following Examples illustrate the present invention in more detail. In these Examples all temperatures are given in degrees Celsius.

EXAMPLE 1

A solution of 0.575 g of 1-[2(R)-[1(R or S)-(benzyloxycarbamoyl)-2-(3,4,4-trimethyl-2,5-dioxo-1-imidazolidinyl)ethyl]-3-cyclopropylpropionyl]piperidine (diastereoisomer 1) in 10 ml of ethanol was hydrogented in the presence of 0.4 g of 5% palladium-on-charcoal catalyst for 6 hours. The catalyst was removed by filtration and the solution was evaporated. The residue was purified by flash chromatography on silica gel using dichloromethane/methanol (96:4) for the elution to give 0.37 g of 1-[3-cyclopropyl-2(R)-[1(R or S)-(hydroxycarbamoyl)-2-(3,4,4-trimethyl-2,5,-dioxo-1-imidazolidinyl)ethyl]propionyl] piperidine (diastereoisomer 1) in the form of a white foam.

nmr (MeOD): 3.78–3.64 (m, 3H); 3.62 (dd, 1H, J=15.8); 3.49–3.41 (m, (1H); 3.39 (dd, 1H, J=15,5); 3.33–3.27 (m, 1H); 2.95–2.87 (m, 1H); 2.83 (s, 3H); 1.74–1.46 (m, 7H); 1.33 (s, 3H); 1.31 (s, 3H); 1.20–1.13 (m, 1H); 0.61–0.50 (m, 1H); 0.44–0.33 (m, 2H); 0.06–0.05 (m, 2H);

MS: 409 $(M+H)^+$.

The starting material was prepared as follows:

(i) A solution of 4.9 g of 2(R)-amino-3-cyclopropylpropionic acid (prepared in a manner analogous to that described by Chenault H. K., Dahmer J. and Whitesides G. M. in J. Am. Chem. Soc. 1989, 111, 6354–6364) in 50 ml of water containing 4.05 ml of concentrated sulphuric acid was warmed to 45°. A solution of 10.5 g of sodium nitrite in 20 ml of water was added dropwise over 30 minutes. The solution was stirred at 45° for 4 hours and then cooled to room temperature. The solution was extracted with three 50 ml portions of ethyl acetate. The combined extracts were washed with water and dried over anhydrous magnesium sulphate. The solvent was evaporated to leave 3.95 g of a yellow oil containing 3-cyclopropyl-2(R)-hydroxypropionic acid which was used in the next step without further purification.

$R_f$ [dichloromethane/methanol (9:1)]=0.65.

(ii) A solution of 3.95 g of the product from (i) in 50 ml of ethyl acetate was treated with 5.32 ml of triethylamine and 3.8 ml of benzyl bromide. The mixture was stirred and heated under reflux for 3 hours, then allowed to cool to room temperature overnight. The suspension was washed with 2M hydrochloric acid, water and saturated sodium chloride solution. After drying over anhydrous magnesium sulphate the solvent was evaporated. The residue was purified by flash chromatography on silica gel using hexane/ethyl acetate (2:1) for the elution to give 3.36 g of benzyl 3-cyclopropyl-2(R)-hydroxypropionate in the form of a yellow oil.

nmr (CDCl$_3$): 7.39–7.28 (m; 5H); 5.19 (d, 1H, J=14); 5.15 (d, 1H, J=14); 4.31–4.24 (m, 1H); 2.81 (br. d, 1H); 1.69–1.54 (m, 2H); 0.87–0.74 (m, 1H); 0.45–0.34 (m, 2H); 0.08–0.07 (m, 2H).

(iii) A solution of 3.36 g of the product from (ii) and 1.49 ml of pyridine in 10 ml of dichloromethane was added dropwise to a solution of 3.07 ml of trifluoromethanesulphonic anhydride in 15 ml of dichloromethane at 0° over 30 minutes with stirring. The mixture was stirred at 0° for 2 hours and then washed with water and saturated sodium chloride solution. After drying over anhydrous magnesium sulphate the solvent was evaporated to give 5.37 g of benzyl 3-cyclopropyl-2(R)-trifluoromethylsulphonyloxypropionate in the form of an orange oil which was used in the next step without further purification.

$R_f$ [hexane/ethyl acetate (4:1)]=0.5.

(iv) A solution of 3.8 g of benzyl tert-butyl malonate in 50 ml of 1,2-dimethoxyethane was treated with 0.504 g of an 80% dispersion of sodium-hydride in mineral oil. The mixture was stirred at room temperature for 30 minutes and then cooled to 0°. A solution of 5.37 g of the product from (iii) in 20 ml of dichloromethane was added dropwise at 0°. The mixture was stirred at 0° for 2 hours and then left to warm to room temperature overnight. The solvent was evaporated and the residue was dissolved in ethyl acetate. The solution was washed with water and saturated sodium chloride solution. After drying over anhydrous magnesium sulphate the solvent was evaporated to give 6.54 g of 2,3-dibenzyl 3-tert-butyl 1-cyclopropyl-2(R),3(R,S),3-propanetricarboxylate as a 1:1 mixture of diastereoisomers in the form of an orange oil.

nmr (CDCl$_3$): 7.46–7.36 (m, 20H); 5.19–5.07 (m, 8.H) 3.89 (d, 1H, J=10); 3.85 (d, 1H, J=10) 3.37–3.26 (m, 2H); 1.68–1.52 (m, 2H); 1.52–1.38 (m, 2H); 1.41 (s, 9H); 1.39 (s, 9H); 0.79–0.63 (m, 2H); 0.49–0.38 (m, 4H); 0.12–0.07 (m, 4H).

(v) A solution of 6.4 g of the product from (iv) in 30 ml of 1,2-dimethoxyethane was treated with 0.446 g of an 80% dispersion of sodium hydride in mineral oil. The mixture was stirred at room temperature for 30 minutes. A solution of 3.84 g of 1-(bromomethyl)-3,4,4-trimethyl-2,5-imidazolinedione in 20 ml of 1,2-dimethoxyethane was added dropwise over 15 minutes. The mixture was stirred at room temperature for 36 hours, the solvent was evaporated and the residue was dissolved in ethyl acetate and washed with water and saturated sodium chloride solution. After drying over anhydrous magnesium sulphate the solvent was evaporated. The residue was purified by flash chromatography on silica gel using hexane/ethyl acetate (7:3) and subsequently hexane/ethyl acetate (6:4) for the elution to give 6.4 g of 2,3-dibenzyl 3-tert-butyl 1-cyclopropyl-4-(3, 4,4-trimethyl-2, 5-dioxo-1-imidazolidinyl)-2(R),3(R,S),3-butanetricarboxylate as a 1:1 mixture of diastereoisomers in the form of a clear oil.

nmr (CDCl$_3$): 7.47–7.28 (m, 20H); 5.31–5.03 (m, 8H); 4.32–4.18 (m, 4H); 3.19–3.15 (m, 1H); 3.16–3.12 (m, 1H); 2.86 (s, 6H); 2.00–1.90 (m, 1H); 1.89–1.79 (m, 1H); 1.64–1.49 (m, 1H); 1.48–1.38 (m, 1H); 1.37 (s, 12H); 1.36 (s, 9H); 1.32 (s, 9H); 0.9–0.8 (m, 2H); 0.41–0.3 (m, 4H); 0.15–0.05 (m, 2H); 0.04–0.04 (m, 2H).

(vi) A solution of 3.0 g of the product from (v) in 30 ml of 2-propanol was hydrogenated in the presence of 0.3 g of 5% palladium on charcoal catalyst for 2 hours. The catalyst was removed by filtration and the solution was evaporated. The residue was re-evaporated from 20 ml toluene and then dissolved in 50 ml of toluene. The solution was treated with 0.693 ml of triethylamine and the mixture was heated under reflux for 2 hours. The solution was cooled to room temperature and washed with 2M hydrochoric acid, water and saturated sodium chloride solution. After drying over anhydrous magnesium suphate the solvent was evaporated to give 1.85 g of 4-tert-butyl hydrogen 2(R)-(cyclopropylmethyl)-3R or S)-[(3,4,4-trimethyl-2,5-dioxo-1-imidazolidinyl)methyl]succinate as an approximately 6:1 mixture of diastereoisomers in the form of a yellow oil.

MS: 383 (M+H)$^+$;

$R_f$ [dichloromethane/methanol (9:1)]=0.41.

(vii) A solution of 1.0 g of the product from (vi) in 10 ml of dichloromethane was cooled to 0° and treated in succession with 0.655 ml of N-ethylmorpholine, 0.481 g of 1-hydroxybenzotriazole and 0.602 g of 1-ethyl-3-(3-dimethylaminopropyl)carbodiimide hydrochloride. The mixture was stirred at 0° for 30 minutes and then treated with 0.517 ml of piperidine. The solution was left to warm to room temperature and was stirred overnight. The solution was washed with 5% aqueous sodium hydrogen carbonate solution, 2M hydrochloric acid and saturated sodium chloride solution. After drying over anhydrous magnesium sulphate the solvent was evaporated to give 1.01 g of of 1-[2(R)-[1(R or S)-(tert-butoxycarbonyl)-2-(3,4,4-trimethyl-2,5-dioxo-1-imidazolidinyl)ethyl]-3-cyclopropylpropionyl]piperidine as an approximately 6:1 mixture of diastereoisomers in the form of a yellow gum.

MS: 450 (M+H)$^+$;

$R_f$ [dichloromethane/methanol (95:5)]=0.51.

(viii) A solution of 1.0 g of the produce from (vii) in 2 ml of trifluoroacetic acid was stirred at room temperature for 2.5 hours. The solvent was evaporated and the residue was re-evaporated from toluene. The residue was dissolved in diethyl ether and the solution was extracted with two portions of 5% aqueous sodium hydrogen carbonate solution. The combined extracts were acidified to pH 2 with concentrated hydrochloric acid and the product was extracted with two portions of dichloromethane. The combined organic extracts were washed with water and saturated sodium chloride solution and dried over anhydrous magnesium sulphate. The solvent was evaporated to give 0.634 g of a white foam containing 1-[2(R)-[1(R or S)-carboxy-2-(3,4, 4-trimethyl-2,5-dioxo-1-imidazolidinyl)ethyl]-3-cyclopropylpropionyl]piperidine as a 6:1 mixture of diastereoisomers which was used in the next step without further purification.

R_f [dichloromethane/methanol (9:1)]=0.31.

(ix) A solution of 0.634 g of the product from (viii) in 10 ml of dichloromethane was cooled at 0°. The solution was treated in succession with 0.41 ml of N-ethylmorpholine, 0.296 g of 1-hydroxybenzotriazole and 0.371 g of 1-ethyl-3-(3-dimethylaminopropyl)carbodiimide hydrochloride. The mixture was stirred at 0° for 30 minutes. A solution of 0.238 g of O-benzylhydroxylamine in 2 ml of dichloromethane was added. The mixture was left to warm to room temperature and was stirred overnight. The solution was washed with two portions of 5% aqueous sodium hydrogen carbonate solution and subsequently with 2M hydrochloric acid, water and saturated sodium chloride solution. After drying over anhydrous magnesium sulphate, the solvent was removed by evaporation. The residue was purified by flash chromatography on silica gel using dichloromethane/methanol (98:2) for the elution to give 0.592 g of 1-[2(R)-[1(R or S)-(benzyloxycarbamoyl)-2-(3,4,4-trimethyl-2,5-dioxo-1-imidazolidinyl)ethyl]-3-cyclopropylpropionyl]piperidine (diastereoisomer 1) as a white foam.

nmr (MeOD); 7.45–7.31 (m, 5H); 4.87 (d, 1H, J=13); 4.79 (d, 1H, J=13); 3.78–3.65 (m, 3H); 3.63 (dd, 1H, J=15, 8); 3.53–3.45 (m, 1H); 3.44 (dd, 1H, J=15,5); 3.34–3.27 (m, 1H); 2.87 (s, 3H); 2.84–2.78 (m, 1H); 1.78–1.49 (m, 7H); 1.49–1.40 (m, 1H); 1.36 (s, 3H); 1.32, (s, 3H); 1.12–1.04 (m, 1H); 0.61–0.50. (m,; 1H); 0.48.–0.37(m, 2H); 0.07–0.06 (m, 2H).

MS: 499 (M+H)⁺.

EXAMPLE 2

In a manner analogous to that described in the first paragraph of Example 1, from 0.391 g of 1-[2(R)-[1(R or S)-(benzyloxycarbamoyl)-2-(3,4,4-trimethyl-2,5-dioxo-1-imidazolidinyl)ethyl]-3-cyclopropylpropionyl]-4-piperidinol (diastereoisomer 1), prepared in a manner analogous to that described in Example 1 (i)–(ix), there was obtained 0.33 g of 1-[3-cyclopropyl-2-(R)-[1(R or S)-(hydroxycarbamoyl)-2-(3,4,4-trimethyl-2,5-dioxo-1-imidazolidinyl)ethyl]propionyl]-4-piperidinol (diastereoisomer 1) in the form of a white foam.

nmr (MeOD): 4.22–4.02 (m, 2H); 3.90–3.81 (m, 1H); 3.69–3.56 (m, 1H); 3.49–3.38(m, 2H); 3.37–3.18 (m, 2H); 3.11–3.01 (m, 1H); 2.97–2.86 (m, 1H); 2.83 (d, 3H, J=5); 2.01–1.78 (m, 2H); 1.68–1.36 (m, 3H); 1.33 (s, 3H); 1.31 (d, 3H, J=5); 1.24–1.13 (m, 1H); 0.62–0.50 (m, 1H); 0.49–0.33 (m, 2H); 0.09–0.05 (m, 2H);

MS: 425 (M+H)⁺.

EXAMPLE 3

In a manner analogous to that described in the first paragraph of Example 1, from 0.822 g of 3-[2(R)-[1(R or S)-(benzyloxycarbamoyl)-2-(3,4,4-trimethyl-2,5-dioxo-1-imidazolidinyl)ethyl]-3-cyclopropyl]-3-azabicyclo[3.2.2]nonane (diastereoisomer 1), prepared in a manner analagous to that described in Example 1 (i)–(ix), there was obtained 0.496 g of 3-[3-cyclopropyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]nonane (diastereoisomer 1) in the form of a white foam.

nmr MeOD): 4.0–3.1(m, 5H); 3.48–3.31 (m, 2H); 2.96–2.86 (m, 1H); 2.82 (s, 3H); 2.14–2.03 (m,2H); 1.80–1.68 (m, 4H); 1.68–1.53(m, 5H); 1.32 (s, 3H); 1.31 (s, 3H); 1.21–1.12.(m, 1H); 0.64–0.52(m, 1H); 0.45–0.33 (m, 2H); 0.08–0.05 (m,2H);

MS: 449 (M+H)⁺.

EXAMPLE 4

In a manner analogous to that described in the first paragraph of Example 1, from 0.6 g of 1-[2(R)-[1(R or S)-(benzyloxycarbamoyl)-2-(3,4,4-trimethyl-2,5-dioxo-1-imidazolidinyl)ethyl]-3-cyclobutylpropionyl]piperidine (diastereoisomer 1), prepared in a manner analogous to that described in Example 1 (i)–(ix), there was obtained 0.5 g of 1-[3-cyclobutyl-2(R)-[1(R or S)-(hydroxycarbamoyl)-2-(3,4,4-trimethyl-2,5-dioxo-1-imidazolidinyl)ethyl]propionyl]piperidine (diastereoisomer 1) in the form of a white foam.

nmr (MeOD): 3.67 (dd, 1H, J=15, 10); 3.64–3.46 (m, 4H); 3.34 (dd, 1H, J=15,8); 3.12 (td, 1H, J=13,3): 2.92–2.84 (m, 1H); 2.82 (s, 3H); 2.22–2.09 (m, 1H); 2.07–1.93 (m, 2H); 1.90–1.42 (m, 12H); (s, 3H); 1.32 (s, 3H)

MS: 423 (M+H)⁺.

EXAMPLE 5

In a manner analogous to that described in the first paragraph of Example 1, from 0.4 g of 1-[2(R)-[1(R or S)-(benzyloxycarbamoyl)-2-(3,4,4-trimethyl-2,5-dioxo-1-imidazolidinyl)ethyl]-3-cyclobutylpropionyl]-4-piperidinol (diastereoisomer 1), prepared in a manner analogous to that described in Example 1 (i)–(ix), there was obtained 0.294 g of 1-[3-cyclobutyl-2(R)-[1(R or S)-(hydroxycarbamoyl)-2-(3,4,4-trimethyl-2,5-dioxo-1-imidazolidinyl)ethyl]propionyl]-4-piperidinol in the form of a white foam.

nmr (MeOD): 4.15–4.05 (m, 1H); 4.04–3.90 (m, 1H); 3.90–3.80 (m, 1H); 3.72–3.57 (m, 1H); 3.45–3.30 (m,2H); 3.18–3.06 (m, 2H); 2.94–2.85 (m, 1H); 2.84 (d, 3H, J=5); 2.21–1.36 (m, 13H); 1.33 (d; 3H, J=3); 1.31 (d, 3H, J=6);

MS: 439 M+H)⁺.

EXAMPLE 6

In a manner analogous to that described in the first paragraph of Example 1, from 0.642 g of 3-[2(R)-[1(R or S)-(benzyloxycaxbamoyl)-2-(3,4,4-trimethyl-2,5-dioxo-1-imidazolidinyl)ethyl]-3-cyclobutyl]-3-azabicyclo[3.2.2]nonane (diastereoisomer 1), prepared in a manner analogous to that described in Example 1 (i)–(ix), there was obtained 0.348 g of 3-[3-cyclobutyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]nonane (diastereoisomer 1) in the form of a white foam.

nmr (MeOD): 3.92 3.83 (m, 2H); 3.76 (dd, 1H, J=15, 13); 3.67–3.57 (m, 2H); 3.34 (dd, 1H, J=15,5); 3.28–3.21 (m, 1H); 2.96–2.87 (m, 1H); 2.83 (s, 3H); 2.23–2.13 (m,1H); 2.12–1.92 (m, 4H); 1.91–1.48 (m, 14H); 1.35(s, 3H); 1.34 (s, 3H).

MS: 463 (M+H)⁺.

EXAMPLE 7

In a manner analogous to that described in the first paragraph of Example 1, from 0.5 g of 1-[2(R)-[1(R or S)-(benzyloxycarbamoyl)-2-(3,4,4-trimethyl-2,5-dioxo-1-imidazolidinyl)ethyl]-3-cyclopentylpropionyl]-4-piperidinol (diastereoisomer 1), prepared in a manner analogous to that described in Example 1 (i)–(ix), there was obtained 0.4 g of 1-[3-cyclopentyl-2[(R)-[1(R or S)-(hydroxycarbamoyl)-2-(3,4,4-trimethyl-2,5-dioxo-1-imidazolidinyl)ethyl]propionyl]-4-piperidinol (diastereoisomer 1) in the form of a white foam.

nmr (MeOD): 4.20–4.02 (m, 2H); 3.91–3.83 (m, 1H); 3.76–3.64 (m, 1H); 3.48–3.32 (m, 2H); 3.26–3.08 (m, 3H); 2.05–1.42 (m, 12H); 1.38–1.25 (m, 7H); 1.18–1.01 (m, 3H);

MS: 453 (M+H)⁺.

EXAMPLE 8

In a manner analogous to that described in the first paragraph of Example 1, From 0.57 g of 3-[2(R)-[1(R or S)-(benzyloxycarbamoyl)-2-(3,4,4-trimethyl-2,5-dioxo-1-imidazolidinyl)ethyl]-3-cyclopentyl]-3-azabicyclo[3.2.2] nonane (diastereoisomer 1), prepared in a manner analogous to that described in Example 1 (i)–(ix), there was obtained 0.48 g of 3-[3-cyclopentyl-2(R)-[1(R or S)-(hydroxycarbamyl)-2-[3,4,4-trimethyl-2,5 -dioxo-1-imidazolidinyl)ethyl]propionyl]-3-azabicyclo[3.2.2]nonane (diastereoisomer 1) in the form of a white foam.

nmr (MeOD): 3.88–3.67 (m, 5H); 3.39–3.31 (m, 2H); 2.92–2.85 (m, 4H); 2.15–2.06 (m, 2H); 1.83–1.45 (m, 16H); 1.36–1.28 (m, 7H; 1.16–1.02 (m, 2H).

EXAMPLE 9

A solution of 0.421 g of an approximately 6:1 mixture of diastereoisomer 1 and diastereoisomer 2 of 1-[2(R)-[1(R or S)-carboxy-2-(3,4,4-trimethyl-2,5-dioxo-1-imidazolidinyl) ethyl]-3-cyclopentylpropionyl]piperidine, prepared in a manner analogous to that described in Example 1(i)–(viii), in 10 ml of dichloromethane was cooled to 0°. The solution was treated with 0.211 g of 1-hydroxybenzotriazole, 0.24 g of 1-ethyl-3-(3-dimethylaminopropyl)carbodiimide hydrochloride and 0.22 ml of N-methylmorpholine. The mixture was stirred at 0° for 15 minutes. A solution of 0.295 g of O-(tert-butyldimethylsilyl)hydroxylamine and 0.22 ml of N-methylmorpholine in 5 ml of dichloromethane was added. The mixture was left to warm to room temperature and was stirred overnight. The solution was washed with two portions of 5% aqueous sodium hydrogen carbonate solution and subsequently with 2M hydrochloric acid and saturated sodium chloride solution. After drying over anhydrous magnesium sulphate, the solvent was evaporated. The residue was purified by flash chromatography on silica gel using dichloromethane/methanol (96:4) for the elution to give 0.123 g of 1-[3-cyclopentyl-2(R)-[1(R or S)-(hydroxycarbamoyl)-2-(3,4,4-trimethyl-2,5-dioxo-1-imidazolidinyl)ethyl]propionyl]piperidine (diastereoisomer 1) in the form of a white foam.

nmr (MeOD): 3.74–3.66 (m, 3H); 3.53–3.45 (m, 2H); 3.34 (dd, J=14.7,1H); 3.23 (dt, J=4, 14, 1H); 2.90–2.84 (m, 4H); 1.80–1.45 (m, 14H); 1.38–1.23 (m, 7H); 1.15–1.01 (m, 2H);

MS: 437 (M+H)⁺.

EXAMPLE 10

In a manner analogous to that described in the first paragraph of Example 1, starting from 0.328 g of 1-[2(R)-[1(R or S)-(benzyloxycarbamoyl)-2-(3,4,4-trimethyl-2,5-dioxo-1-imidazolidinyl)ethyl]-3-cyclohexylpropionyl] piperidine (diastereoisomer 1), prepared in a manner analogous to that described in Example 1(i)–(ix), there was obtained 0.269 g of 1-[3-cyclohexyl-2(R)-[1(R or S)-(hydroxycarbamoyl)-2-(3,4,4-trimethyl-2,5-dioxo-1-imidazolidinyl)ethyl]propionyl]piperidine (diastereoisomer 1) in the form of a white foam.

nmr (MeOD): 3.87–3.77 (m, 2H); 3.7 (dd, J=14,9,1H); 3.64–3.56 (m, 2H); 3.38–3.28 (m, 2H); 2.9–2.83 (m, 4H);
1.84–1.45 (m, 12H); 1.35(s, 3H); 1.33 (s, 3H); 1.25–1.05 (m, 5H); 0.98–0.78 (m, 2H).

MS: 451 (M+H)⁺.

EXAMPLE 11

In a manner analogous to that described in Example 9, starting from 0.8 g of 1-[2(R)-[1(R or S)-carboxy-2-(3,4,4-trimethyl-2,5-dioxo-1-imidazolidinyl)ethyl]-3-cyclopentylpropionyl]-tetrahydro-1,4-thiazine (diastereoisomer 1), prepared in a manner analogous to Example 1 (i)–(viii), there was obtained 0.3 g of 4-[3-cyclopentyl-2(R)-[1-(R or S)-(hydroxycarbamoyl)-2-(3,4,4-trimethyl-2,5-dioxo-1-imidazolidinyl)ethyl]propionyl]-tetrahydro-1,4-thiazine (diastereoisomer 1) in the form of a white foam.

nmr (MeOD): 4.02–3.96 (m, 2H); 3.92–3.85 (m, 2H); 3.7 (dd, J=13,9,1H); 3.37 (dd, J=13,6,1H); 3.25–3.18 (m, 1H); 2.9–2.84 (m, 4H); 2.82–2.75 (m, 1H); 2.7–2.55 (m, 3H); 1.78–1.45 (m, 8H); 1.35 (s, 3H); 1.34 (s, 3H); 1.18–1.04 (m, 2H).

MS: 455 (M+H)⁺.

EXAMPLE 12

In a manner analogous to that described in Example 1, starting from 0.3 g of 4-[2(R)-[1(R or S)-(benzyloxycarbamoyl)-2-(3,4,4-trimethyl-2,5-dioxo-1-imidazolidinyl)ethyl]-3-cyclopentylpropionyl]-tetrahydro-1,4-thiazine S,S-dioxide (diastereoisomer 1), prepared in a manner analogous to that described in Example 1 (i)–(ix), there was obtained 0.2 g of 4-[3-cyclopentyl-2(R)-[1-(R or S)-(hydroxycarbamoyl)-2-(3,4,4-trimethyl-2,5-dioxo-1-imidazolidinyl)ethyl]propionyl]-tetrahydro-1,4-thiazine S,S dioxide (diastereoisomer 1) in the form of a white solid.

nmr (MeOD): 4.45–4.3 (m, 2H); 4.0–3.93 (m, 1H) 3.78–3.65 (m, 2H); 3.55–3.39 (m, 2H); 3.30–3.21 (m, 2H); 3.14–3.03 (m, 2H); 2.9–2.85 (m, 4H); 1.78–1.45 (m, 9H); 1.36 (s, 3H); 1.34 (s, 3H); 1.18–1.0 (m, 2H).

MS: 487 (M+H)⁺.

EXAMPLE 13

In a manner analogous to that described in Example 9, starting from 0.8 g of 1-[2(R)-[1(R or S)-carboxy-2-(3,4,4-trimethyl-2,5-dioxo-1-imidazolidinyl)ethyl]-3-cyclobutylpropionyl]-tetrahydro-1,4-thiazine (diastereoisomer 1), prepared in a manner analogous to Example 1 (i)–(viii), there was obtained 0.24 g of 4-[3-cyclobutyl-2(R)-[1-(R or S)-(hydroxycarbamoyl)-2-(3,4,4-trimethyl-2,5-dioxo-1-imidazolidinyl)ethyl]propionyl]-tetrahydro-1,4-thiazine (diastereoisomer 1) in the form of a white solid.

nmr (MeOD): 3.98–3.75 (m, 4H); 3.64 (dd, J=13,8,1H); 3.35 (dd, J=15,6,1H); 3.07 (td, J=10,4,1H); 2.9–2.83 (m, 1H); 2.82 (s, 3H); 2.78–2.72 (m, 1H); 2.66–2.52 (m, 3H); 2.18–2.08 (m, 1H); 2.05–1.93 (m, 2H); 1.85–1.45 (m, 6H); 1.13 (s, 3H); 1.11 (s, 3H).

MS: 441 (M+H)⁺.

EXAMPLE 14

In a manner analogous to that described in Example 9, starting from 1.22 g of 1-[2(R)-[1-(R or S)-carboxy-2l-(3,4,4-trimethyl-2,5-dioxo-1-imidazolidinyl)ethyl]-3-cyclohexylpropionyl]-tetrahydro-1,4-thiazine (diastereoisomer 1), prepared in a manner analogous to Example 1(i)–(viii), there was obtained 0.45 g of 4-[3- cyclohexyl-2(R)-[1(R or S)-(hydroxycarbamoyl)-2-(3,4,4-trimethyl-2,5-dioxo-1-imidazolidinyl)ethyl]propionyl]-tetrahydro-1,4-thiazine (diastereoisomer 1) in the form of a white solid.

nmr (MeOD): 4.12–4.03 (m, 2H); 3.95–3.88 (m, 1H); 3.75–3.65 (m, 2H); 3.38 (dd, J=14,6,1H); 2.88–2.82 (m; 4H); 2.78–2.72 (m, 1H); 2.68–2.55 (m, 3H); 1.82–1.53 (m, 7H); 1.35 (s, 3H); 1.34 (s, 3H); 1.26–0.8 (m, 8H);

MS: 469 (M+H)$^+$.

EXAMPLE 15

In a manner analogous to that described in Example 9, from 1.164 g of a mixture of diastereoisomers of 3-[2(R)-[1(RS)-carboxy-2-(3,4,4-trimethyl-2,5-dioxo-1-imidazolidinyl)ethyl]-3-cyclopentylpropionyl]-5,5-dimethyl-N-propyl-4(R)-thiazolidinecarboxamide, prepared in a manner analogous to that described in Example 1 (i)–(viii), there was obtained 0.329 g of 3-[3-cyclopentyl-2(R)-[1(R or S)-(hydroxycarbamoyl)-2-(3,4,4-trimethyl-2,5-dioxo-11-imidazolidinyl)ethyl]propionyl]-5,5-dimethyl-N-propyl-4(R)-thiazolidinecarboxamide (diastereoisomer 1) in the form of a white solid.

nmr (MeOD): 5.09–4.72 (m, 2H); 4.51 and 4.46 (both s, total 1H); 3.84 and 3.64 (both dd, J=14,8,1H); 3.40–3.05 (m, 4H); 2.90–2.73 (m, 4H); 1.94–1.25 (m, 23H); 1.23–1.01 (m, 2H); 0.99–0.85 (m, 3H); MS: 554 (M+H)$^+$.

EXAMPLE 16

In a manner analogous to that described in the first paragraph of Example 1, from 0.223 g of 4-[2(R)-[R or S)-(benzyloxycarbamoyl)-2-(3,4,4-trimethyl-2,5-dioxo-1-imidazolidinyl)ethyl]-3-cyclopentylpropionyl]morpholine (diastereoisomer 1), prepared in a manner analogous to that described in Example 1 (i)–(ix), there was obtained 0.112 g of 4-[3-cyclopentyl-2(R)-[1(R or S)-(hydroxycarbamoyl)-2-(3,4,4-trimethyl-2,5-dioxo-1-imidazolidinyl)ethyl]propionyl]morpholine (diastereoisomer 1) in the form of white solid.

nmr (MeOD): 3.83–3.56 (m, 9H); 3.41 (dd, J=14,6, 1H); 3.19 (dt, J=4,11,1H); 2.91–2.81 (m, 4H); 1.77–1.42 (m, 8H); 1.38–1.23 (m, 7H); 1.19–0.99 (m, 2H);

MS: 439 (M+H)$^+$.

EXAMPLE 17

In a manner analogous to that described in Example 9, from 1.289 g of a mixture of diastereoisomers of 3-[2(R)-[1(RS)-carboxy-2-(3,4,4-trimethyl-2,5-dioxo-1-imidazolidinyl)ethyl]-3-cyclopentylpropionyl]-N,5,5-trimethyl-4(R)-thiazolidinecarboxamide (diastereoisomer 1), prepared in a manner analogous to that described in Example 1 (i)–(viii), there was obtained 0.629 g of 3-[3-cyclopentyl-2(R)-[1(R or S)-(hydroxycarbamoyl)-2-(3,4,4-trimethyl-2,5-dioxo-1-imidazolidinyl)ethyl]propionyl]-N,5,5-trimethyl-4(R)-thiazolidinecarboxamide (diastereoisomer 1) in the form of a white solid.

nmr (MeOD): 4.09–4.51 (m, 2H); 4.47 and 4.43 (both s, total 1H); 3.82 and 3.62 (both dd, J=14,10, total 1H); 3.37 and 3.17 (both dd, J=14,5, total 1H); 3.13–2.70 (m, 8H); 1.96–1.25 (m, 21H); 1.23–0.99 (m, 2H);

MS: 526 (M+H)$^+$.

EXAMPLE 18

In a manner a analogous to that described in the first paragraph of Example 1, from 0.289 g of 1-[2(R)-[1(R or S)-(benzyloxycarbamoyl)-2-(3,4,4-trimethyl-2,5-dioxo-1-imidazolidinyl)ethyl]-3-cyclobutylpropionyl]-4l-phenylpiperazine (diastereoisomer 1), prepared in a manner analogous to that described in Example 1 (i)–(ix), there was obtained 0.121 g of 1-[3-cyclobutyl-2(R)-[1(R or S)-[(hydroxycarbamoyl)methyl]-2-(3,4,4-trimethyl-2,5-dioxo-1-imidazolidinyl)ethyl]propionyl]-4-phenylpiperazine (diastereoisomer 1) in the form of a white solid.

nmr (MeOD): 7.25 (m, 2H); 7.00 (m, 2H); 6.85 (m, 1H); 3.94–3.73 (m, 4H); 3.66 (dd, J=14,7,1H); 3.43 (dd, J=14,6, 1H); 3.23–3.09 (m, 4H); 2.96–2.84 (m, 1H); 2.84 (s, 3H); 2.27–2.13 (m, 1H); 2.09–1.95 (m, 2H); 1.90–1.48 (m, 6H); 1.35 (s, 3H); 1.34 (s, 3H);

MS:499 (M)$^+$.

EXAMPLE 19

In a manner analogous to that described in the first paragraph of Example 1, from 0.455 g of 4-[2(R)-[1(R or S)-benzyloxycarbamoyl)-2-(3,4,4-trimethyl-2,5-dioxo-1-imidazolidinyl)ethyl]-3-cyclobutylpropionyl]morpholine (diastereoisomer 1), prepared in a manner analogous to that described in Example 1 (i)–(ix), there was obtained 0.194 g of 4-[3-cyclobutyl-2(R)-[1(R or S)-(hydroxycarbamoyl)-2-(3,4,4-trimethyl-2,5-dioxo-1-imidazolidinyl)ethyl]propionyl]morpholine (diastereoisomer 1) in the form of a white solid.

nmr (MeOD): 3.80–3.51 (m, 9H); 3.42 (dd, J=14,6,1H); 3.14–3.06 (dt, J=4,11,1H); 3.04–2.86 (m, 1H); 2.85 (s, 3H); 2.23–2.11 (m, 1H); 2.06–1.95 (m, 2H); 1.91–1.73 (m, 2H); 1.71–1.46 (m, 4H); 1.35 (s, 3H); 1.34 (s, 3H); MS:425 (M)$^+$.

EXAMPLE 20

In a manner analogous to that described in the first paragraph of Example 1, from 0.625 g of 1-[2(R)-[1(R or S)-benzyloxycarbamoyl)-2-(3,4,4-trimethyl-2,5-dioxo-1-imidazolidinyl)ethyl]-3-cyclobutylpropionyl]pyrrolidine (diastereoisomer 1), prepared in a manner analogous to that described in Example 1 (i)–(ix), there was obtained 0.384 g of 1-[3-cyclobutyl-2(R)-[1(R or S)-(hydroxycarbamoyl)-2-(3,4,4-trimethyl-2,5-dioxo-1-imidazolidinyl)ethyl]propionyl]morpholine diastereoisomer 1) in the form of a white solid.

nmr (MeOD): 3.77–3.69 (m, 1H); 3.61 (dd, J=14,6,1H); 3.53–3.44 (m, 2H); 3.39–3.31 (m, 2H); 2.93–2.85 (m, 2H); 2.84 (s, 3H); 2.26–2.13 (m, 1H); 2.07–1.71 (m, 8H); 1.69–1.46 (m, 4H); 1.36 (s, 3H); 1.33 (s, 3H); MS:409 (M+H)$^+$.

EXAMPLE 21

In a manner analogous to that described in the first paragraph of Example 1, from 0.176 g of 8-[2(R)-[1(R or S)-benzyloxycarbamoyl)-2-(3,4,4-trimethyl-2,5-dioxo-1-imidazolidinyl)ethyl]-3-cyclobutylpropionyl]-1,4-dioxa-8-azaspiro[4,5]decane (diastereoisomer 1), prepared in a manner analogous to that described in Example 1 (i)–(ix), there was obtained 0.084g of 8-[3-cyclobutyl-2(R)-[1(R or S)-(hydroxycarbamoyl)-2-(3,4,4-trimethyl-2,5-dioxo-1-imidazolidinyl)ethyl]propionyl]-1,4-dioxa-8-azaspiro[4,5]decane (diastereoisomer 1) in the form of a white solid.

nmr (MeOD): 4.02 (s, 4H); 3.81–3.60 (m, 5H); 3.99 (dd, J=14,6,1H); 3.20–3.10 (m, 1H); 2.93–2.85 (m, 1H); 2.84 (s, 3H); 2.21–2.09 (m, 1H); 2.06–1.93 (m, 2H); 1.80–1.46 (m, 10H); 1.35 (s, 3H); 1.33 (s, 3H);

MS :481 (M+H)$^+$.

EXAMPLE 22

In a manner analogous to that described in the first paragraph of Example 1, from 0.443 g of 1-[2(R)-[1(R or S)-benzyloxycarbamoyl)-2-(3,4,4-trimethyl-2,5-dioxo-1-imidazolidinyl)ethyl]-3-cyclobutylpropionyl]-4-methoxypiperidine (diastereoisomer 1) there was obtained 0.319 g of 1-[3-cyclobutyl-2(R)-[1(R or S)-(hydroxycarbamoyl)-2-(3,4,4-trimethyl-2,5-dioxo-1-imidazolidinyl)ethyl]propionyl]-4-methoxypiperidine (diastereoisomer 1) in the form of a white solid.

nmr (MeOD): 3.96–3.0 (m, 2H); 3.69–3.59 (m, 1H); 3.54–3.23 (m, 7H); 3.18–3.09 (m, 1H); 2.93–2.80 (m, 4H); 2.21–2.09 (m, 1H); 2.07–1.41 (m, 12H); 1.41–1.38 (m, 6H);

MS:453 (M+H)$^+$.

The starting material was prepared as follows
(i) A solution of 0.925 g of 1-[2(R)-[1(R or S)-(tert.butoxycarbonyl)-2-(3,4,4-trimethyl-2,5-dioxo-1-imidazolidinyl)ethyl]-3-cyclopropylpropionyl]-4-hydroxypiperidine in 8 ml of dimethylformamide was treated with 1.08 g of methyl iodide and 1.79 g of silver oxide. The mixture was stirred at room temperature in the dark for 2 days. Additional portions of 0.54 g of methyl iodide and 0.895 g of silver oxide were then added and the mixture was stirred for a further 3 days. The solvent was evaporated and the residue was suspended in ethyl acetate and filtered. The ethyl acetate solution was concentrated and the residue was purified by flash chromatography on silica gel using ethyl acetate for the elution. There was obtained 0.61 g of 1-[2(R)-[1(R or S)-(tert.butoxycarbonyl)-2-(3,4,4-trimethyl-2,5-dioxo-1-imidazolidinyl)ethyl]-3-cyclobutylpropionyl]-4-methoxypiperidine in the form of a colorless gum.

(ii) In a manner: analogous to that described in Example 1 (viii)–(ix) from 0.61 g of 1-[2(R)-[1(R or S)-(tert.butoxycarbonyl)-2-(3,4,4-trimethyl-2,5-dioxo-1-imidazolidinyl)ethyl]-3-cyclobutylpropionyl]-4-methoxypiperidine there was obtained 0.443 g of 1-[2(R)-[1(R or S)-(benzyloxycarbamoyl)-2-(3,4,4-trimethyl-2,5-dioxo-1-imidazolidinyl)ethyl]-3-cyclobutylpropionyl]-4-methoxypiperidine (diastereoisomer 1) in the form of a colorless gum.

EXAMPLE 23

In a manner analogous to that described in the first paragraph of Example 1, from 0.94 g of 1-[2(R)-[1(RS)-benzyloxycarbonoyl)-2-(3,4,4-trimethyl-2,5-dioxo-1-imidazolidinyl)ethyl]-3-cyclobutylpropionyl]-octahydroazocine diastereoisomer 1), prepared in a manner analogous to that described in Example 1 (i)–(ix), there was obtained 0.663 g of 1-[3-cyclobutyl-2(R)-[1(R or S)-hydroxycarbamoyl)-2-(3,4,4-trimethyl-2,5-dioxo-1-imidazolidinyl)ethyl]propionyl]octahydroazocine (diastereoisomer 1) in the form of a white solid:

nmr (MeOD): 3.77 (dd, J=14,10,1H); 3.66–3.43 (m, 4H); 3.33 (dd, J=14,5,1H); 3.07 (dt, J=10,4,1H); 2.91–2.81 (m, 4H); 2.29–2.16 (m, 1H); 2.10–1.95 (m, 2H); 1.90–1.46 (m, 16H); 1.34 (s, 6H);

MS:451(M+H)$^+$.

EXAMPLE 24

In a manner analogous to that described in the first paragraph of as Example 1, from 0.37 g of 1-[2(R)-[1(R or S)-benzyloxycarbamoyl)-2-(5,5-dimethyl-2,4-dioxo-3-oxazolidinyl)ethyl]-3-cyclobutylpropionyl]piperidine (diastereoisomer 1), prepared in a manner analogous to that described in Example 1 (v)–(ix) using 3-(bromomethyl)-5,5-dimethyloxazolidine-2,4-dione in place of 1-(bromomethyl)-3,4,4-trimethyl-2,5-imidazolinedione, there was obtained 0.131 g of 1-[3-cyclobutyl-2(R)-[1(R or S)-(hydroxycarbamoyl)-2-(5,5-dimethyl-2,4-dioxo-3-oxazolidinyl)ethyl]propionyl]piperidine (diastereoisomer 1) in the form of a white solid:

nmr (MeOD): 3.72–3.53 (m, 5H): 3.39 (dd, J=14,6,1H), 3.14 (dt, J=10,4,1H); 2.95–2.86 (m, 1H); 2.23–2.11 (m, 1H); 2.08–1.94 (m, 2H); 1.90–1.44 (m, 18H);

MS:410 (M+H)$^+$.

EXAMPLE 25

In a manner analogous to that described in the first paragraph of Example 1, from 0.42 g of 1-[2(R)-[1(R or S)-benzyloxycarbamoyl)-2-(3,4,4-trimethyl-2,5-dioxo-1-imidazolidinyl)ethyl]-3-cyclobutylpropionyl] hexahydroazepine (diastereoisomer 1), prepared in a manner analogous to that described in Example 1 (i)–(ix), there was obtained 0.197 g of 1-[3-cyclobutyl-2(R)-[1(R or S)-(hydroxycarbamoyl)-2-(3,4,4-trimethyl-2,5-dioxo-1-imidazolidinyl)ethyl]propionyl]hexahydroazepine (diastereoisomer 1) in the form of a white solid:

nmr (MeOD): 3.77–3.64 (m, 2H); 3.62–3.45 (m, 3I-I); 3.33 (dd, J=14,5,1H); 3.07 (dt, J=10,4,1H); 2.91–2.81 (m, 4H); 2.24–2.13 (m, 1H); 2.09–1.95 (m, 2H); 1.90–1.47 (m, 14H); 1.35 (s, 3H); 1.34 (s, 3H);

MS:437 (M+H)$^+$.

EXAMPLE 26

In a manner analogous to that described in the first paragraph of Example 1, from 0.37 g of 1-[2(R)-[1(R or S)-benzyloxycarbamoyl)-2-(hexahydro-1,3-dioxopyrazolo[1,2-a][1,2,4]triazol-2-yl)ethyl]-3-cyclobutylpropionyl] piperidine (diastereoisomer 1), prepared in a manner analogous to that described in Example 1 (i)–(ix), using 2-(bromomethyl)-hexahydro-1,3-dioxopyrazolo[1,2-a][1,2,4]triazole, there was obtained 0.118 g of 1-[3-cyclobutyl-2 (R)-[2-(hexahydro-1,3-dioxopyrazolo[1,2-a][1,2,4]triazol-2-yl)-1(R or S)-(hydroxycarbamoyl)ethyl]propionyl] piperidine in the form of a white solid.

nmr (MeOD): 3.68–3.56 (m,8H); 3.52–3.39 (m,2H); 3.17–3.09 (m,1H); 2.97–2.90 (m,1H); 2.35–2.27 (m,2H); 2.21–2.11 (m,1H); 2.07–1.95 (M,2H) 1.88–1.44 (m,12H) MS:422 (M+H)$^+$.

EXAMPLE 27

In a manner analogous to that described in the first paragraph of Example 1, from 0.222 g of 1-[2(R or S)-(benzyloxycarbamoyl)-2-phthalimidoethyl]-3-cyclobutylpropionyl]piperidine prepared in a manner analogous to that described in Example 1(i)–(ix) using N-(bromomethyl)-phthalimide, there was obtained 0.013 g of 1[3-cyclobutyl-(2(R)-[1(R or S)-(hydroxycarbamoyl)-2-phthalimidoethyl]propionyl]piperidine (diastereoisomer 1) in the form of a white solid.

nmr (MeOD): 7.87–7.75 (m,4H); 3.83 (dd,J=14.8,1H); 3.66–3.58 (m,3H); 3.53–3.45 (m,1H); 3.35–3.25 (m,1H); 3.20–3.12 (m,1H); 3.04–2.97 (m,1H); 2.23–2.11 (m,1H); 2.08–1.95 (m,2H); 1.89–1.41 (m,12H); MS:428 (M+H)$^+$ The following Examples illustrate pharmaceutical preparations containing the hydroxamic acid derivatives provided by the present invention:

EXAMPLE A

Tablets containing the following ingredients may be produced in a conventional manner:

| Ingredient | Per tablet |
|---|---|
| Hydroxamic acid derivative | 10.0 mg |
| Lactose | 125.0 mg |
| Corn starch | 75.0 mg |
| Talc | 4.0 mg |
| Magnesium stearate | 1.0 mg |
| Total weight | 215.0 mg |

EXAMPLE B

Capsules containing the following ingredients may be produced in a conventional manner:

| Ingredient | Per capsule |
|---|---|
| Hydroxamic acid derivative | 10.0 mg |
| Lactose | 165.0 mg |
| Corn starch | 20.0 mg |
| Talc | 5.0 mg |
| Capsule fill weight | 200.0 mg |

We claim:

1. Compounds of the formula

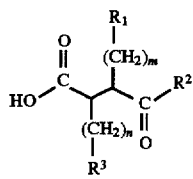

(II)

wherein $R^1$ represents cyclopropyl, cyclobutyl, cyclopentyl or cyclohexyl;

$R^2$ represents a saturated 5- to 8-membered monocyclic or bridged N-heterocyclic ring, which N-heterocyclic ring is attached via the N atom and when it is monocyclic, optionally contains $NR^4$, O, S, SO or $SO_2$ as a ring member and/or is optionally substituted on one or more C atoms by hydroxy, lower alkyl, lower alkoxy, oxo, ketalized oxo, amino, mono(lower alkyl)amino, di(lower alkyl)amino, carboxy, lower alkoxycarbonyl, hydroxymethyl, lower alkoxymethyl, carbamoyl, mono(lower alkyl)-carbamoyl, di(lower alkyl)carbamoyl or hydroxyimino;

$R^3$ is of the formula selected from the group consisting of

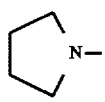 (a)

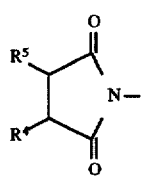 (b)

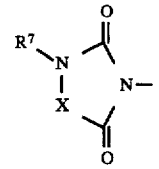 (c)

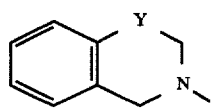 (d)

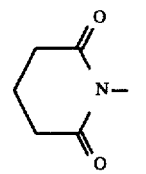 (e)

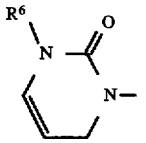 (f)

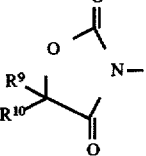 (g)

and

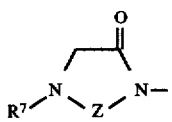 (h)

$R^4$ represents hydrogen, lower alkyl, aryl, aralkyl or a protecting group;

m stands for 1 or 2;

n stands for an integer from 1 to 4;

$R^5$ and $R^6$ each represents hydrogen or together represent an additional bond or the remainder of a fused benzene ring;

$R^7$ represents hydrogen, lower alkyl or aryl;

X represents —CO—, —$CH_2$—, —CH(lower alkyl)—, —C(lower alkyl)$_2$—, —NH—, —N(lower alkyl)— or —O—;

$R^8$ represents hydrogen, lower alkyl or aryl;

$R^9$ and $R^{10}$ each represent hydrogen or lower alkyl;

Y represents —O—, —NH— or —N(lower alkyl)—; and

Z represents S, SO or $SO_2$;

wherein lower alkyl and aryl is as hereinbefore defined; and pharmaceutically acceptable salts thereof.

* * * * *

UNITED STATES PATENT AND TRADEMARK OFFICE
CERTIFICATE OF CORRECTION

Page 1 of 2

PATENT NO. : 5,731,441
DATED : March 24, 1998
INVENTOR(S) : Michael John Broadhurst, et. al.

It is certified that error appears in the above-indentified patent and that said Letters Patent is hereby corrected as shown below:

In claim 1, column 21, lines 56-59, replace Figure (a) with

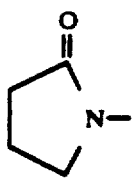

In claim 1, column 22, lines 10-14, replace Figure (d) with

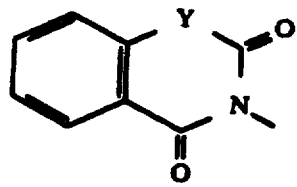

UNITED STATES PATENT AND TRADEMARK OFFICE
CERTIFICATE OF CORRECTION

PATENT NO. : 5,731,441
DATED : March 24, 1998
INVENTOR(S) : Michael John Broadhurst, et. al.

It is certified that error appears in the above-indentified patent and that said Letters Patent is hereby corrected as shown below:

In claim 1, column 22, lines 21-27, replace Figure (f) with

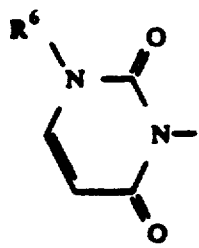

Signed and Sealed this

Twenty-eighth Day of July, 1998

*Attest:*

BRUCE LEHMAN

*Attesting Officer*     Commissioner of Patents and Trademarks